US005500002A

United States Patent [19]

Riddle et al.

[11] Patent Number: 5,500,002

[45] **Date of Patent: *Mar. 19, 1996**

[54] CONTINOUS PASSIVE MOTION PHYSICAL THERAPY DEVICE

[75] Inventors: George E. Riddle, Clinton; Ronnie J. Withrow, Athens; George M. Cox, LaFollette, all of Tenn.

[73] Assignee: United Apothecary, Inc., Oak Ridge, Tenn.

[ * ] Notice: The term of this patent shall not extend beyond the expiration date of Pat. No. 5,320,640.

[21] Appl. No.: 247,248

[22] Filed: May 23, 1994

Related U.S. Application Data

[63] Continuation-in-part of Ser. No. 843,805, Feb. 28, 1992, Pat. No. 5,320,640, and Ser. No. 9,788, Jan. 27, 1993, Pat. No. 5,320,641.

[51] Int. Cl.[6] .......... A61F 5/00

[52] U.S. Cl. .......... 606/242; 606/243; 5/617

[58] Field of Search .......... 606/242, 243, 606/241, 245; 5/613, 617, 636, 607; 61/33

[56] References Cited

U.S. PATENT DOCUMENTS

| | | |
|---|---|---|
| 1,190,195 | 7/1916 | Schmidt . |
| 1,628,369 | 5/1927 | McBurney . |
| 1,830,071 | 11/1931 | Patton . |
| 2,002,349 | 5/1935 | Lundeen . |
| 2,104,745 | 1/1938 | Howell et al. . |
| 2,152,431 | 3/1939 | Jensen . |
| 2,179,595 | 11/1939 | McManis . |
| 2,598,204 | 5/1952 | Allen . |
| 2,749,911 | 6/1956 | Griffin . |
| 2,865,367 | 12/1958 | Sorenson . |
| 2,931,354 | 4/1960 | Sellner . |
| 3,241,828 | 3/1966 | Adolphson et al. . |
| 3,315,666 | 4/1967 | Sellner . |
| 3,450,132 | 6/1969 | Ragon et al. . |
| 3,623,480 | 11/1971 | Chisholm . |
| 3,640,272 | 2/1972 | Hussey . |
| 3,674,017 | 7/1972 | Stefani, Jr. . |
| 3,741,200 | 6/1973 | Morin . |
| 4,144,880 | 3/1979 | Daniels . |
| 4,245,626 | 1/1981 | Paolino . |
| 4,379,450 | 4/1983 | Sjölinder . |
| 4,419,989 | 12/1983 | Herbold . |
| 4,445,504 | 5/1984 | Barge . |
| 4,531,730 | 7/1985 | Chenera . |
| 4,649,905 | 3/1987 | Barnes . |
| 4,655,200 | 4/1987 | Knight . |
| 4,691,694 | 9/1987 | Boyd et al. . |
| 4,723,537 | 2/1988 | Parker, Jr. . |
| 4,724,828 | 2/1988 | Barnes et al. . |
| 4,798,197 | 1/1989 | Nippoldt et al. . |
| 4,817,940 | 4/1989 | Shaw et al. . |

(List continued on next page.)

*Primary Examiner*—Linda C. M. Dvorak
*Attorney, Agent, or Firm*—Pitts & Brittian

[57] ABSTRACT

A continuous passive motion physical therapy device for passively exercising the muscle groups especially surrounding the lumbar spine for postoperative and other rehabilitative therapy. An improved pivoting support displacement device, comprised of first and second actuators, for oscillating at least one pivoting support member is provided. The first actuator is associated with the upper torso support member and includes an output cam for imparting substantially linear motion to a connecting rod. The connecting rod is pivotally secured to one end of the output cam and at a selected location to an actuator cam. The actuator cam is secured to the axle to which is releasably secured a displacement cam. A push rod is releasably and pivotally secured between the displacement cam and the upper torso support member. The second actuator is associated with the lower body support member and includes an actuator cam and a displacement cam, each being substantially similar to those of the first actuator. Further, the second actuator includes a second connecting rod having opposite ends thereof pivotally connected to the distal ends of the actuator cams of the first and second actuators. Thus, as the actuator cam of the first actuator is oscillated, the actuator cam of the second actuator is simultaneously oscillated.

11 Claims, 4 Drawing Sheets

U.S. PATENT DOCUMENTS

| | | |
|---|---|---|
| 4,827,913 | 5/1989 | Parker . |
| 4,834,072 | 5/1989 | Goodman . |
| 4,869,494 | 9/1989 | Lambert, Sr. . |
| 4,888,581 | 12/1989 | Guscott . |
| 4,890,092 | 12/1989 | Grimm . |
| 4,900,014 | 2/1990 | DeGraff . |
| 4,953,541 | 9/1990 | Parker, Jr. . |
| 4,957,286 | 9/1990 | Persons, II et al. . |
| 4,960,111 | 10/1990 | Steffensmeier . |
| 5,014,688 | 5/1991 | Fast . |
| 5,023,967 | 6/1991 | Ferrand . |
| 5,044,359 | 9/1991 | Reinert . |
| 5,054,774 | 10/1991 | Belsito . |
| 5,098,089 | 3/1992 | Harrington et al. . |
| 5,099,828 | 3/1992 | Duke . |
| 5,107,822 | 4/1992 | Ohashi . |
| 5,123,916 | 6/1992 | Riddle et al. . |
| 5,138,729 | 8/1992 | Ferrand . |
| 5,158,568 | 10/1992 | Riddle et al. . |
| 5,171,260 | 12/1992 | McIlwain . |
| 5,258,019 | 11/1993 | Riddle et al. . |

CONTINOUS PASSIVE MOTION PHYSICAL THERAPY DEVICE

DESCRIPTION

This is a Continuation-in-Part patent application based upon patent application Ser. No. 07/843,805 filed Feb. 28, 1992, now U.S. Pat. No. 5,320,640 and upon patent application Ser. No. 08/009,788 filed Jan. 27, 1993, now U.S. Pat. No. 5,320,641, both of which are based upon a parent patent application Ser. No. 07/640,945, filed on Jan. 14, 1991, which has matured into U.S. Pat. No. 5,123,916 issued Jun. 23, 1992.

TECHNICAL FIELD

The present invention relates generally to physical therapy machines, particularly those used in the field of post-trauma and post-operative spinal therapy. Specifically, this invention relates to an apparatus used in the postoperative rehabilitation of the cervical spine to regain strength and function.

BACKGROUND ART

In the field of spinal therapy, it is well known that serious loss of motion, painful contractures and stiffness may occur. Further, it is also well known rehabilitation is difficult in that the normal collagen formation cannot occur and disorganized scar results which further impedes the healing process recovery.

Various devices have been developed by which spinal portion of the human body can be exercised for rehabilitative purposes. These devices have also been utilized in other, but related, exercise of the body to strengthen muscle tone, etc., even when there has been no operation. Typical of the devices developed for this field are those disclosed in the following U.S. Patents:

| U.S. Pat. No. | Inventor(s) | Issue Date |
|---|---|---|
| 1,190,195 | M. Schmidt | Jul 4, 1916 |
| 1,628,369 | M. R. McBurney | May 10, 1927 |
| 1,830,071 | W. T. Patton | Nov 3, 1931 |
| 2,002,349 | E. F. Lundeen | May 21, 1935 |
| 2,104,745 | H. H. Howell, et al. | Jan 11, 1938 |
| 2,152,431 | S. H. Jensen | Mar 28, 1939 |
| 2,179,595 | J. V. McManis | Nov 14, 1939 |
| 2,598,204 | R. E. Allen | May 27, 1952 |
| 2,749,911 | L. Griffin | Jun 12, 1956 |
| 2,865,367 | D. L. Sorenson | Dec 23, 1958 |
| 2,931,354 | J. W. Sellner | Apr 5, 1960 |
| 3,241,828 | R. T. Adolphson, et al. | Mar 22, 1966 |
| 3,315,666 | J. W. Sellner | Apr 25, 1967 |
| 3,450,132 | C. A. Ragon, et al. | Jun 17, 1969 |
| 3,623,480 | R. F. Chisholm | Nov 30, 1971 |
| 3,640,272 | J. L. Hussey | Feb 8, 1972 |
| 3,674,017 | H. Stefani, Jr. | Jul 4, 1972 |
| 3,741,200 | H. Morin | Jun 26, 1973 |
| 4,144,880 | E. R. Daniels | Mar 20, 1979 |
| 4,379,450 | P. O. Sjölinder | Apr 12, 1983 |
| 4,419,989 | T. E. Herbold | Dec 13, 1983 |
| 4,445,504 | F. H. Barge | May 1, 1984 |
| 4,531,730 | R. Chenera | Jul 30, 1985 |
| 4,649,905 | J. E. Barnes | Mar 17, 1987 |
| 4,655,200 | A. C. Knight | Apr 7, 1987 |
| 4,691,694 | R. L. Boyd, et al. | Sep 8, 1987 |
| 4,723,537 | A. E. Parker, Jr. | Feb 9, 1988 |
| 4,724,828 | J. E. Barnes, et al. | Feb 16, 1988 |
| 4,798,197 | R. H. Nippoldt, et al. | Jan 17, 1989 |
| 4,817,940 | B. F. Shaw, et al. | Apr 4, 1989 |
| 4,827,913 | A. E. Parker | May 9, 1989 |
| 4,834,072 | L. M. Goodman | May 30, 1989 |

-continued

| U.S. Pat. No. | Inventor(s) | Issue Date |
|---|---|---|
| 4,869,494 | T. E. Lambert, Sr. | Sep 26, 1989 |
| 4,888,581 | J. K. Guscott | Dec 19, 1989 |
| 4,890,092 | V. A. Grimm | Dec 26, 1989 |
| 4,900,014 | A. H. DeGraff | Feb 13, 1990 |
| 4,953,541 | A. E. Parker, Jr. | Sep 4, 1990 |
| 4,957,286 | C. A. Persons, II, et al. | Sep 18, 1990 |
| 4,960,111 | L. A. Steffensmeier | Oct 2, 1990 |
| 5,014,688 | D. Fast | May 14, 1991 |
| 5,023,967 | R. Ferrand | Jun 18, 1991 |
| 5,044,359 | O. C. Reinert | Sep 3, 1991 |
| 5,054,774 | A. W. Belsito | Oct 8, 1991 |
| 5,098,089 | J. J. Harrington, et al. | Mar 24, 1992 |
| 5,099,828 | C. H. Duke | Mar 31, 1992 |
| 5,107,822 | K. Ohashi | Apr 28, 1992 |
| 5,123,916 | G. E. Riddle, et al. | Jun 23, 1992 |
| 5,138,729 | R. Ferrand | Aug 18, 1992 |
| 5,158,568 | G. E. Riddle, et al. | Oct 27, 1992 |
| 5,171,260 | W. A. McIlwain | Dec 15, 1992 |
| 5,258,019 | G. E. Riddle, et al. | Nov 2, 1993 |

Each of these devices was disclosed in the prosecution of one or more of the aforementioned U.S. patent application Ser. Nos. 07/843,805 filed Feb. 28, 1992; 08/009,788 filed Jan. 27, 1993; and 07/640,945, filed on Jan. 14, 1991, which has matured into U.S. Pat. No. 5,123,916 issued Jun. 23, 1992, or in the prosecution of U.S. patent application Ser. No. 07/693,674 filed Apr. 30, 1991 which has matured into U.S. Pat. No. 5,158,568; and 07/902,084 filed Jun. 22, 1992 which has matured into U.S. Pat. No. 5,258,019. The device of the present invention and the devices disclosed in these five patent applications, three of which have issued and the other two of which have been allowed and are due to issue, were invented by at least one common inventor. In the background art statements and in the prosecution of each of the previously filed patent applications, the above-referenced prior art has been distinguished. The discussions of the prior art and the subject matter disclosed in each of these prior applications are incorporated herein by reference.

With respect to the present application, those devices of interest include those devices previously disclosed by the present inventors and those devices disclosed by Daniels U.S. Pat. No. (4,144,880) and Knight U.S. Pat. No. (4,655,200). In the '880 device, a motor is used to rotate a disc-shaped plate, to which one end of a drive shaft is eccentrically and pivotally secured. The other end of the drive shaft is connected to one end of a connecting rod. As the motor is operated, the drive shaft is motivated back and forth in a substantially horizontal direction such that the connecting rod oscillates through a specific angle, the connecting rod being pivotally connected proximate its center to the frame. This oscillation in turn causes the upper platform frame 18 to oscillate via the long connecting rod 70 and the lower platform frame 34 is oscillated via the crank arm 64.

The '200 device incorporates a jack including a screw-type actuator driven by a motor to simultaneously raise and lower a pair of bell cranks, thus simultaneously raising and lowering both ends of the therapy table.

Neither of these devices, however, disclose the use of a single drive motor to simultaneously oscillate at least two support surfaces, while allowing the independent variation of the degree of motion of each of the support surfaces. Further, these devices do not disclose the use of such a device for the passive therapy of the muscle groups especially surrounding the lumbar spine for postoperative and other rehabilitative therapy.

Therefore, it is an object of this invention to provide a means for passively exercising the muscle groups especially surrounding the lumbar spine for postoperative and other rehabilitative therapy.

Another object of this invention is to provide a means whereby at least two support surfaces may be oscillated simultaneously and at equal rates, while the degree of oscillation of each being independently selectable.

DISCLOSURE OF THE INVENTION

Other objects and advantages will be accomplished by the present invention which is an improvement of the devices of the above-referenced patent applications by the present inventors, each of which serves to passively exercise the muscle groups especially surrounding the lumbar spine for postoperative and other rehabilitative therapy. In accordance with the present invention, there is provided an improved pivoting support displacement device for oscillating at least one pivoting support member. Specifically, the pivoting support displacement device of the present invention includes first and second actuators associated with the upper torso support member and the lower body support member, respectively. The first actuator includes an output cam for imparting substantially linear motion to a connecting rod. The connecting rod is pivotally secured to one end of the output cam and at a selected location to an actuator cam associated with the first actuator. The actuator cam is secured to the axle to which is also secured in a releasable fashion a displacement cam. A push rod is releasably and pivotally secured to the displacement cam.

As the transmission output shaft is rotated the actuator cam is rotated and the displacement cam is rotated such that the push rod is raised or lowered and the associated support member is elevated or lowered accordingly.

The second actuator includes an actuator cam and a displacement cam, each being substantially similar to those of the first actuator. Further, the second actuator includes a second connecting rod having opposite ends thereof pivotally connected to the distal ends of the actuator cams of the first and second actuators. Thus, as the actuator cam of the first actuator is oscillated, the actuator cam of the second actuator is simultaneously oscillated. The displacement cams associated with the first and second actuators may be selectively oriented to be in-phase or out of phase.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

Figure 1:
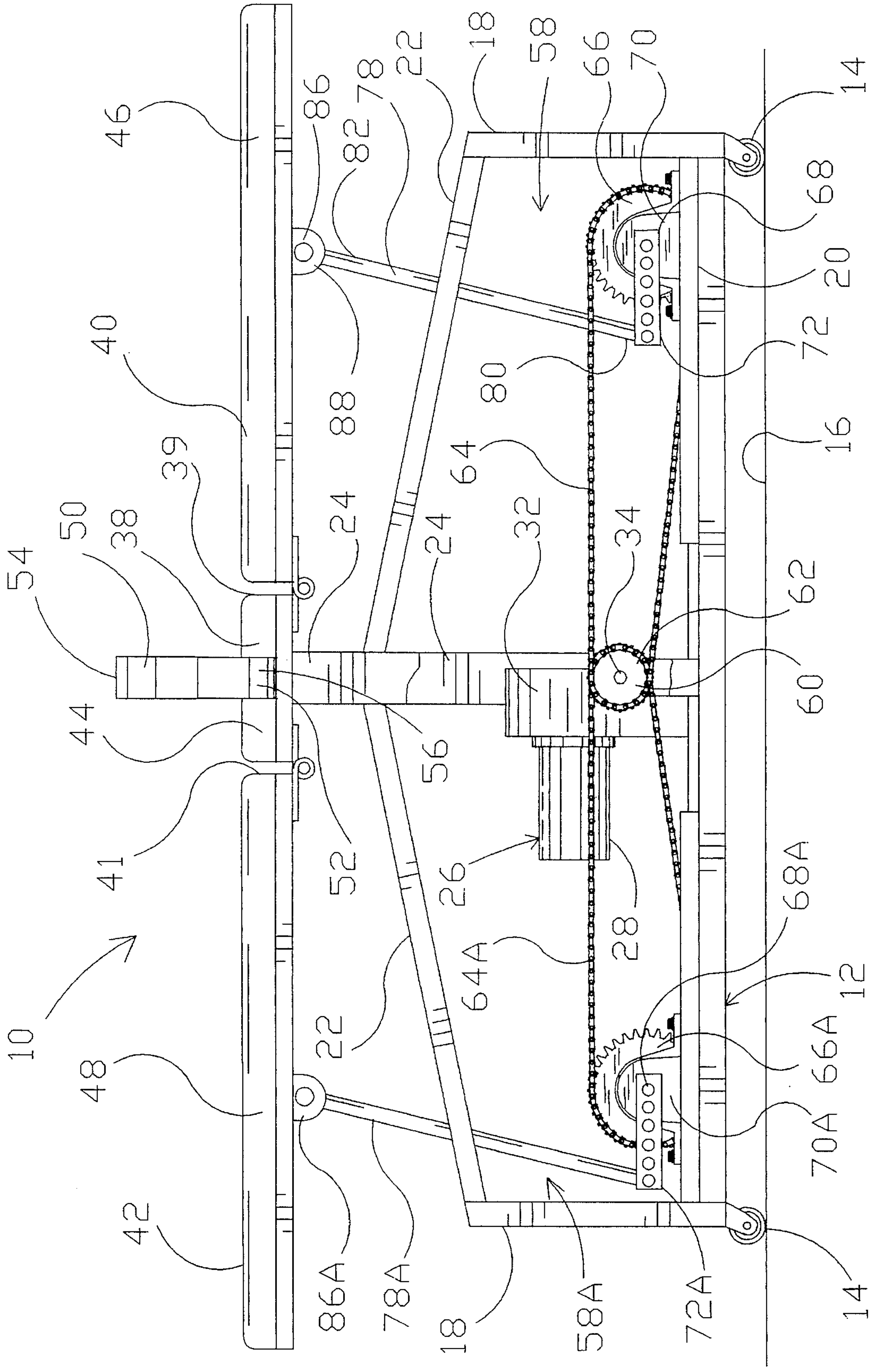
FIG. 1 is a front elevational view of the continuous passive motion physical therapy device constructed in accordance with several features of the present invention.
Figure 2:
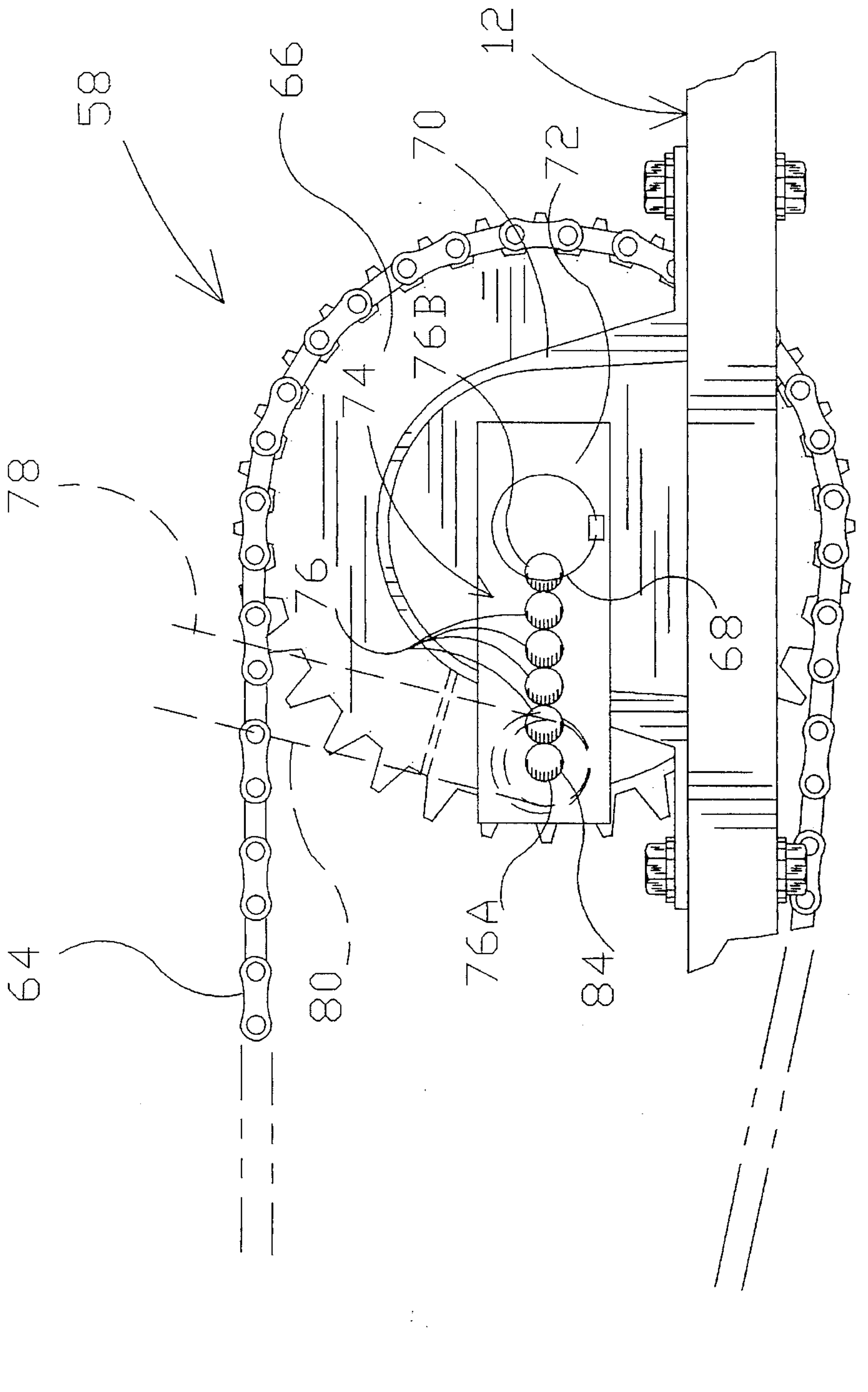
FIG. 2 illustrates a partial front elevation view of the continuous passive motion physical therapy device of FIG. 1 more clearly showing the actuator of a preferred embodiment, the push rod being shown in phantom.

The present invention, in one embodiment, is illustrated generally at 10 in FIGS. 1 and 2. This embodiment is of particular application for lumbar spine therapy. There is a frame member 12 which, in this embodiment, includes caster members 14 for support upon a building floor 16. The caster members permit movement of the device from place to place within a building. It will be recognized, however, the frame member 12 can be provided with feet (not shown) to rest directly on the floor 16. The frame member 12 typically is formed from a plurality of vertical leg members 18 that are interconnected with a plurality of horizontal members 20. Further, there typically are angular brace members 22. The leg members 18, the horizontal members 20 and the angular brace members 22 typically are fabricated from either tubular or angle stock. Also, the frame member 12 typically includes vertical brace members 24 (only one shown) generally centrally located on opposite long sides of the frame member 12.

Mounted upon the frame member 12 are various body support members. For example, there is a substantially centrally-located body support member 38 for the support of the buttocks of a patient, this portion 38 is in a fixed position on the frame member 12. Hingedly attached to the frame along one long edge of the fixed support member 38, as at 39, is an upper torso support member 40, and a lower body support member 42 is hingedly attached to an opposite side edge of the fixed member 38, as at 41. The fixed body support 38, and the supports 40, 42 for the torso and lower body of the patient are typically provided with pads 44, 46 and 48, respectively. Typically, a patient restraint 50 is provided proximate a center of the device. This restraint typically is a belt member 52 with a clasp 54 to adjust fit to the patient. Opposite ends of the belt member 52 are fixed to the fixed support member 38 as at 56.

Elevation and depression of the torso support member 40 relative to a horizontal orientation is effected by an actuator 58. In the embodiment illustrated in FIGS. 1 and 2, a second actuator 58A is utilized to pivotally elevate or depress a lower body support portion 42. This is substantially identical to actuator 58. It will be understood that a third actuator (not shown) can be used if the lower body support 42 is split into two leg support portions (not shown) as described in the afore-cited U.S. patent application Ser. No. 07/902,084.

In the illustrated embodiments, a drive means 26 is provided for operating each of the actuators 58 in order to simultaneously oscillate the upper torso support member 40 and the lower body support member 42. The drive means 26 is powered by a selected motor 28 commonly used in the art. In the preferred embodiment, the rotational velocity of the motor 28 may be variably controlled. The drive shaft 30 of the motor 28 is connected through a transmission 32 to at least one actuator The transmission 32 is provided for controlling the rotational velocity of an output shaft 34 in relation to the rotational velocity of the motor 28.

In the embodiment illustrated in FIGS. 1 and 2, each actuator 58 includes a pinion carried by the output shaft 34 of the transmission 32. The pinion 60 includes a sprocket 62 configured to engage a chain 64. A gear 66 is in turn driven by the chain 64. An axle 68 extends from the center of the gear and is journaled to a plurality of support blocks 70, each support block 70 being secured to the frame 12 in a conventional fashion. In the preferred embodiment, the axle 68 is journaled to at least two support blocks 70, at least one support block 70 being located on either side of the gear 66 to limit the axle to rotational movement.

A displacement cam 72 is releasably secured to the axle 68, the displacement cam thus rotating as the gear 66 is rotated. The securement of the displacement cam 72 to the axle 68 may be any conventional method whereby the orientation of the displacement cam 72 with respect to the axle 68 is variable. The first end 80 of a push rod 78 is journaled to the displacement cam 72 eccentrically such that as the displacement cam 72 is rotated, the first end 80 of the push rod 78 is moved in a circular direction. In the preferred embodiment, the displacement cam 72 defines at least one threaded opening 76 dimensioned to receive a selected bolt 84. The first end of the push rod 78 has a substantial "eye" configuration dimensioned to loosely receive the selected bolt 84 inserted into the cam The second end 82 of the push rod 78 is journally connected to the bottom side of the associated support member 40,42 a distance from the support member hinged end 39,40 so that as the first end 80 of the push rod 78 is moved in a circular motion, the second end 82 of the push rod 78 and the associated support member 40,42 are displaced vertically. The second end 82 of the push rod 78 of the preferred embodiment has a substantial "eye" configuration and is dimensioned to be received by a clevis 86 and held in place with a selected pin 88, bolt or the like.

As previously disclosed in the aforementioned patent applications, the push rod 78 may be fabricated from various sections which may be disconnected by the operator of the device as a safety precaution. An observer may selectively disengage a particular support member 40,42 simply by holding the distal end thereof and lifting upward. The resulting disconnection of the separate sections of the push rod 78 ceases the displacement of the associated support member 40,42 from the operation of the motor 28.

A displacement adjuster 74 is carried by each displacement cam 72 for selectively and independently altering the amplitude of displacement of the upper torso support member 40 and the lower body support member 42. In the preferred embodiment, a plurality of openings 76 is defined by the displacement cam 72, the openings 76 being spaced apart radially away from the axle 68. The openings 76 are threaded to receive the selected bolt 84 used to attach the push rod 78 as described above. The opening 76A spaced farthest from the axle 68 has the greatest eccentricity and therefore will yield the greatest displacement of the associated support member 40,42. Likewise, the opening 76B spaced closest to the axle 68 is the least eccentric and will therefore yield the least displacement. As disclosed in the afore-mentioned U.S. Pat. No. 5,158,568, it is envisioned that the displacement adjuster 74 may alternatively be connected to the support member 40,42 proximate the push rod second end 82, the amplitude adjustment being a resultant of varying the distance between the push rod second end 82 and the support member hinged end 39,41.

The relative orientation of the displacement cams 72,72A may be varied with respect to each other (or to the second and third displacement cams when a third pivoting support member is incorporated.) This may be accomplished by rotating the displacement cam 72,72A associated with one of the actuators 58,58A while maintaining the other of the displacement cams 72,72A in a locked position. When the relative orientations of the displacement cams 72,72A are as desired, each is then locked in place in relation to the other. Thus, the phase of the upper torso support member 40 and the lower body support member 42 may be in-phase to enable both to be raised simultaneously, or out of phase to enable one of the upper torso support member 40 and the lower body support member 42 to be raised while the other is lowered.

In similar fashion to the illustrated embodiment, in the above-cited embodiment wherein the lower body support member 42 is split into two leg support portions, second and third actuators (not shown) are used independently one from the other and can hence be moved in-phase or out-of-phase with respect to each other and with respect to the displacement cam 72 associated with the upper torso support member 40.

Figure 3:
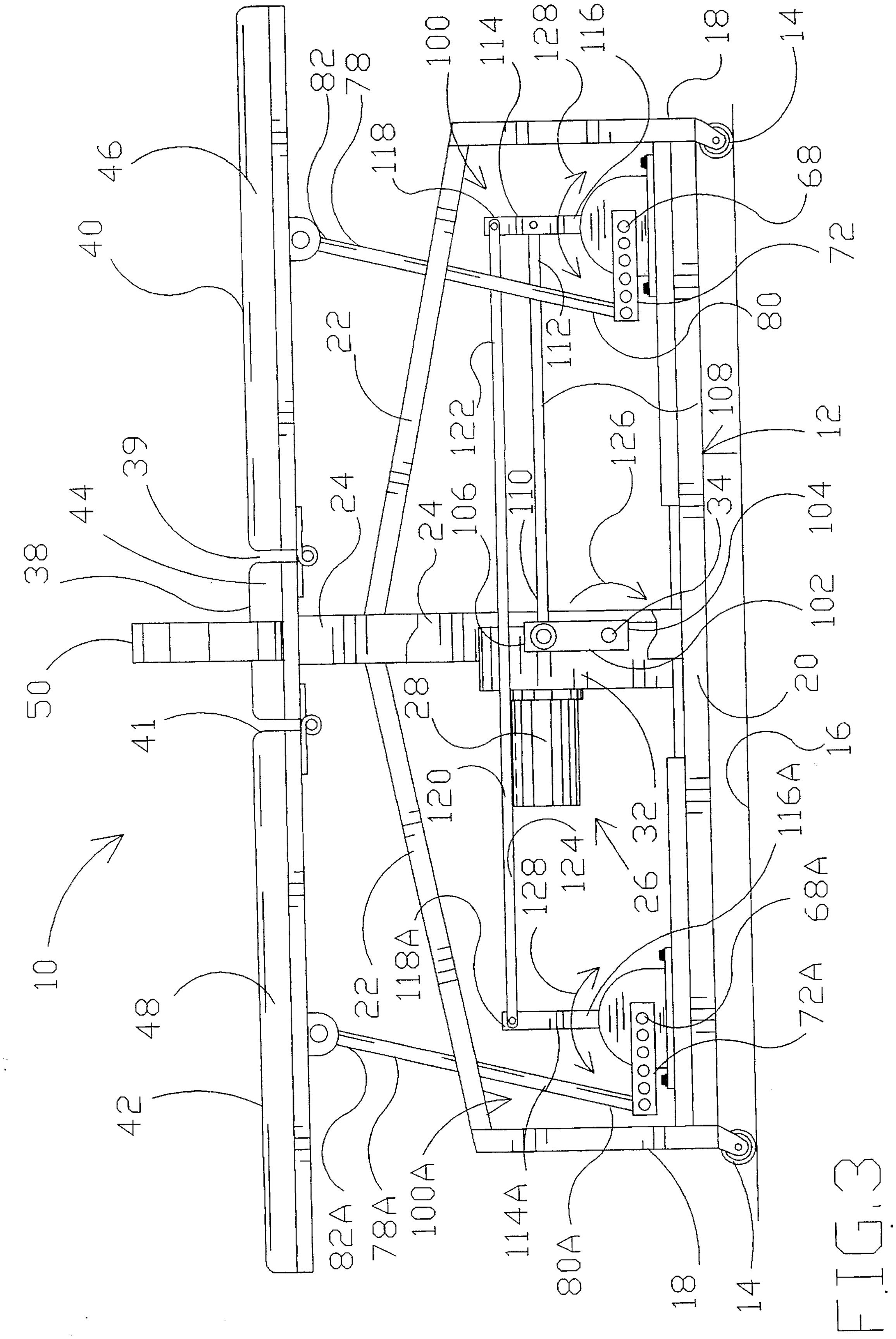
FIG. 3 is a front elevational view of an alternate embodiment of the continuous passive motion physical therapy device constructed in accordance with several features of the present invention.
Figure 4:
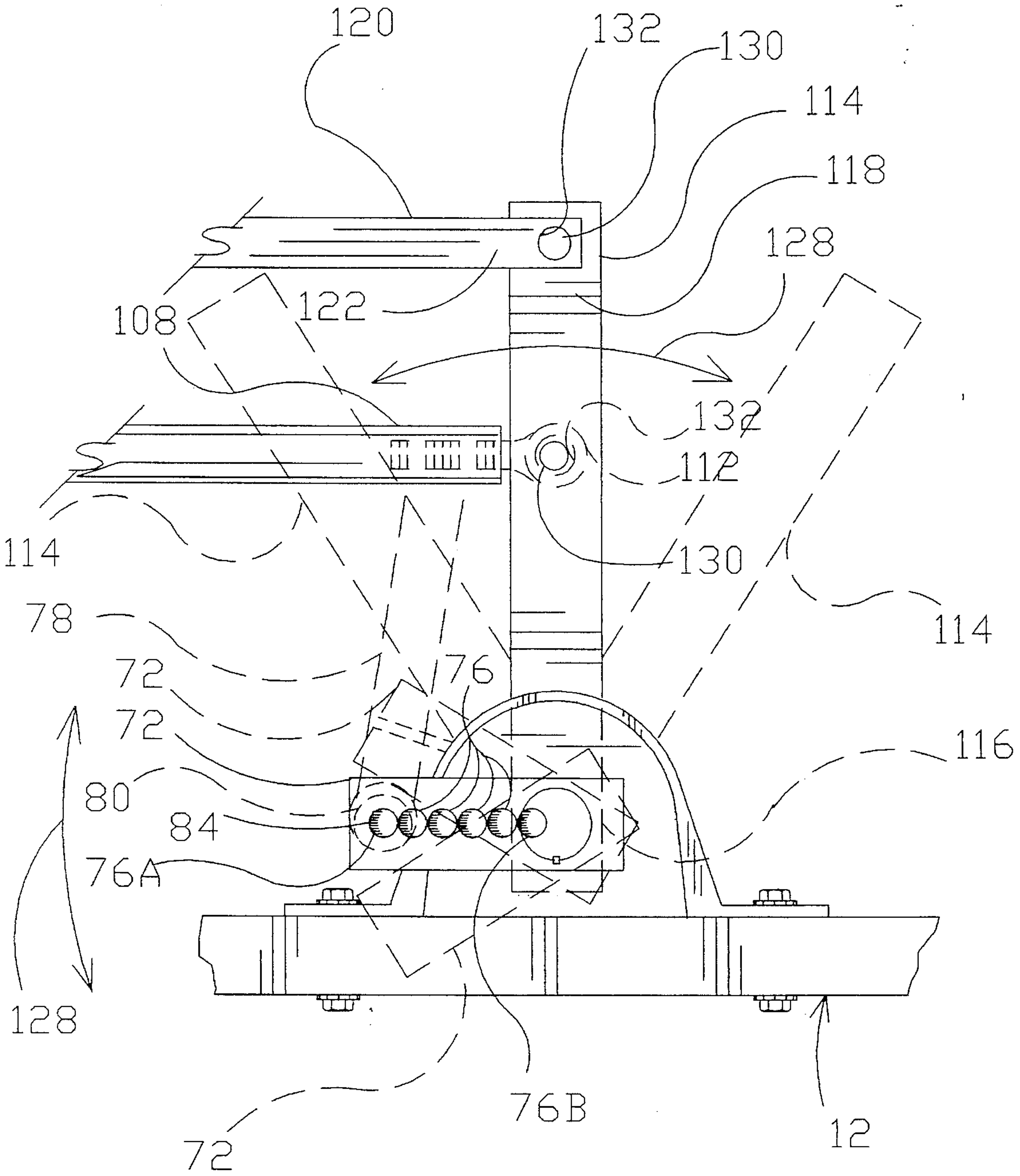
FIG. 4 illustrates a partial front elevation view of the continuous passive motion physical therapy device of FIG. 3 more clearly showing the actuator of a preferred embodiment, the push rod being shown in phantom.

In the embodiment illustrated in FIGS. 1 and 2, and described above, as the motor 28 is operated, the end result is the rotation of the displacement cam 72, the vertical displacement of the push rod 78, and ultimately the oscillation of the upper torso support member 40 and/or the lower body support member 42. An alternative to this embodiment wherein the same motor 28 may be used in substantially the same manner to yield substantially the same displacement of the upper torso support member 40 and the lower body support member 42 is illustrated in FIGS. 3 and 4. In this embodiment, substantially all of the elements described heretofore may be incorporated, with the exception of the actuators 58.

In the alternate embodiment of FIGS. 3 and 4, a first actuator 100 is associated with the upper torso support member 40 and a second actuator 100A is associated with the lower body support member 42. The first actuator 1OO includes an output cam 102, the proximal end 104 of which is secured to the transmission output shaft 34. The proximal end 110 of a first connecting rod 108 is pivotally secured to the distal end 106 of the output cam 102. The distal end 112 of the first connecting rod 108 extends away from the output cam 102 and is pivotally secured at a selected location to an actuator cam 114. The proximal end 116 of the actuator cam 114 is secured to the axle 68 in similar fashion as the gear 66 in the previously-described embodiment. The displacement cam 72 is releasably secured to the axle 68 as also previously described.

As illustrated, when the actuator cam 114 is in a substantially vertical orientation, the displacement cam 72 is oriented in a substantially horizontal position. In the illustrated orientation, as the output shaft 34 is rotated in a clockwise direction, as indicated by the arrow 126, the output cam 102 is rotated accordingly, thus rotating the proximal end 110 of the first connecting rod 108. Due to the connection of the distal end 112 of the first connecting rod 108 to the actuator cam 114, the first connecting rod distal end 112 is limited to an arcuate movement about the axis of rotation of the axle 68, as indicated by the double-headed arrow 128. Hence, the actuator cam 114, the axle and the displacement cam 72 are each oscillated about the axis of rotation of the axle 68 through a predetermined angle. Although not depicted, this predetermined angle through which these elements are rotated, and most importantly the displacement cam 72, may be varied by varying the location on the actuator cam 114 at which the first connecting rod distal end 112 is pivotally secured. Moving the connection closer to the axle 68 will increase the range of motion, and vice versa.

The push rod 78 is secured to the displacement cam 72 as in the previous embodiments. Thus, as the transmission output shaft 34 is rotated clockwise from the illustrated orientation, the actuator cam 114 is rotated to the right of vertical, and the displacement cam 72 is rotated such that the push rod 78 is raised and the upper torso support member 40 is elevated at an angle above the horizontal. By reorienting the displacement cam 72 with respect to the axle one hundred eighty degrees (180°), this same rotation of the transmission output shaft 34 would result in the lowering of the upper torso support member 40 to an angle below the horizontal.

The second actuator 100A includes an actuator cam 114A and a displacement cam 72A, each being substantially similar to those of the first actuator 100. Further, the second actuator 100A includes a second connecting rod 120 having opposite ends 122,124 thereof pivotally connected to the distal ends of the actuator cams 114,114A of the first and second actuators 100,100A. Thus, as the actuator cam 114 of the first actuator 100 is oscillated, the actuator cam 114A of the second actuator 100A is simultaneously oscillated.

The displacement cams 72,72A associated with the first and second actuators 100,100A, respectively, may be selectively oriented to be in-phase or out of phase as in the embodiment of FIGS. 1 and 2. Further, it is envisioned that the lower body support member 42 may be split to embody two leg supports (not shown). In this embodiment, a further displacement cam (not shown) is secured to the axle 68A, preferably at an opposite end with respect to the illustrated displacement cam 72A. Thus the phase relationship of the individual leg support members may be selected in substantially the same manner as previously described.

As described, the proximal end 110 of the first connecting rod 108 is pivotally connected to the output cam 102, the distal end 112 of the first connecting rod 108 is pivotally connected to the actuator cam 114 of the first actuator 100, and the ends 122,124 of the second connecting rod 120 are pivotally connected to the distal ends 118,118A of each of the actuator cams 114,114A. Each of these pivotal connections may be made in a conventional manner. Typically, however, a stud 130 is carried in a conventional manner by the output cam 102 or actuator cam 114,144A. The stud 130 is received within an opening 132 defined by the particular connecting rod end 110,112,122,124, the opening 132 being defined in a conventional manner as by securing an eye-bolt to the connecting rod end 110,112,122,124 or by drilling.

From the foregoing description, it will be recognized by those skilled in the art that a lumbar spine therapy device offering advantages over the prior art has been provided. Specifically, the present invention provides an inventive method of oscillating the pivoting support members of a lumbar spine therapy device, which in turn provides a means for passively exercising the muscle groups especially surrounding the lumbar spine for post-operative and other rehabilitative therapy such as to allow normal collagen formation to occur, thus minimizing scarring and allowing a faster return to normal function and development of strength in both the muscles of function as well as the secondary support system.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention,

We claim:

1. A device for continuous passive motion physical therapy, said device comprising:

a frame member for structurally supporting said device and any loads applied thereto;

a stationary support member secured to said frame member for supporting the buttocks of a user;

at least one pivoting support member for supporting at least a selected portion of a user's body, said at least one pivoting support member being hingeably attached about one end to said frame member proximate one side of said stationary support member;

at least one actuator for pivoting said at least one pivoting support member about said one end, one of said at least one actuator being in association with one of said at least one pivoting support member;

a drive mechanism for simultaneously driving each of said at least one actuator, said drive mechanism including a selected motor with a drive shaft connected to said at least one actuator, said actuator including an output cam fixed at its distal end to said drive shaft, a first connecting rod being journally connected at its proximal end to a distal end of said output cam and at its distal end to a first actuator cam between the proximal and distal ends thereof, said first actuator cam being fixed at its said proximal end to a first axle secured to said frame member, and a first displacement cam being releasably secured to said first axle; and a first push rod being journally connected at its proximal end to said first displacement cam and at its distal end to said at least one pivoting support member.

2. The device of claim 1 wherein said at least one pivoting support member includes an upper torso support member for supporting at least a portion of the torso of a user and a lower body support member for supporting at least the upper legs of a user.

3. The device of claim 2 wherein said at least one actuator includes a first actuator associated with said upper torso support member and a second actuator associated with said lower body support member, said first actuator comprising said output cam, said first connecting rod, said first actuator cam, said first axle, and said first displacement cam, said second actuator comprising a second actuator cam substantially identical to said first actuator cam and fixed at its proximal end to a second axle secured to said frame member, said second axle being substantially identical to said first axle, a second displacement cam substantially identical to said first displacement cam and releasably secured to said second axle, and a second connecting rod journally connected at its proximal end to a distal end of said second actuator cam and at its distal end to said distal end of said first actuator cam, said first push rod being journally connected at its said distal end to said upper torso support member, said device further comprising a second push rod substantially identical to said first push rod and journally connected at its proximal end to said second displacement cam and at its distal end to said lower body support member.

4. The device of claim 3 wherein each of said first and second displacement cams define a plurality of openings for attaching said proximal end of said first and second push rods, respectively, said openings being spaced linearly away from said first and second axles for varying an eccentricity of said first and second push rod proximal ends with respect to said first and second axles, thereby varying a degree of motion of said upper torso and lower body support members, respectively.

5. The lumbar spine therapy device of claim 4 wherein said degree of motion of each of said upper torso and lower body support members is variable independently one from the other.

6. A device for continuous passive motion physical therapy, said device comprising:

a frame member for structurally supporting said device and any loads applied thereto;

a stationary support member secured to said frame member for supporting the buttocks of a user;

an upper torso support member for supporting at least a portion of the torso of a user, said upper torso support member being hingeably attached about one end to said frame member proximate one side of said stationary support member;

a lower body support member for supporting at least a portion of the upper legs of a user, said upper torso support member being hingeably attached about one end to said frame member proximate one side of said stationary support member;

a first actuator for pivoting said upper torso support member about said one end;

a second actuator for pivoting said lower body support member about said one end;

a drive mechanism for simultaneously driving each of said first and second actuators, said drive mechanism including a selected motor with a drive shaft connected to said first actuator, said first actuator including an output cam fixed at its distal end to said drive shaft, a first connecting rod being journally connected at its proximal end to a distal end of said output cam and at its distal end to a first actuator cam between the proximal and distal ends thereof, said first actuator cam being fixed at its said proximal end to a first axle secured to said frame member, and a first displacement cam being releasably secured to said first axle, said second actuator comprising a second actuator cam substantially identical to said first actuator cam fixed at its proximal end to a second axle secured to said frame member, said second axle being substantially identical to said first axle, a second displacement cam substantially identical to said first displacement cam releasably secured to said second axle, and a second connecting rod journally connected at its proximal end to a distal end of said second actuator cam and at its distal end to said distal end of said first actuator cam, said first push rod being journally connected at its said distal end to said upper torso support member;

a first push rod journally connected at its proximal end to said first displacement cam and at its distal end to said upper torso support member; and a second push rod journally connected at its proximal end to said second displacement cam and at its distal end to said lower body support member.

7. The device of claim 6 wherein each of said first and second displacement cams define a plurality of openings for attaching said proximal end of said first and second push rod, respectively, said openings being spaced linearly away from said first and second axles for varying an eccentricity of said first and second push rod proximal ends with respect to said first and second axles, thereby varying a degree of motion of said upper torso and lower body support members, respectively.

8. The device of claim 6 wherein said degree of motion of each of said upper torso and lower body support members is variable independently one from the other.

9. A device for continuous passive motion physical therapy, said device comprising:

a frame member for structurally supporting said device and any loads applied thereto;

a stationary support member secured to said frame member for supporting the buttocks of a user;

an upper torso support member for supporting at least a portion of the torso of a user, said upper torso support member being hingeably attached about one end to said frame member proximate one side of said stationary support member;

a lower body support member for supporting at least a portion of the upper legs of a user, said upper torso support member being hingeably attached about one end to said frame member proximate one side of said stationary support member;

a first actuator for pivoting said upper torso support member about said one end;

a second actuator for pivoting said lower body support member about said one end;

a drive mechanism for simultaneously driving each of said first and second actuators, said drive mechanism including a selected motor with a drive shaft connected to said first actuator, said first actuator including an output cam fixed at its distal end to said drive shaft, a first connecting rod being journally connected at its proximal end to a distal end of said output cam and at its distal end to a first actuator cam between the proximal and distal ends thereof, said first actuator cam being fixed at its said proximal end to a first axle secured to said frame member, and a first displacement cam being releasably secured to said first axle, said first displacement cam defining a plurality of openings spaced linearly away from said first axle, said second actuator comprising a second actuator cam substantially identical to said first actuator cam fixed at its proximal end to a second axle secured to said frame member, said second axle being substantially identical to said first axle, a second displacement cam substantially identical to said first displacement cam releasably secured to said second axle, said second displacement cam defining a plurality of openings spaced linearly away from said second axle, and a second connecting rod journally connected at its proximal end to a distal end of said second actuator cam and at its distal end to said distal end of said first actuator cam, said first push rod being journally connected at its said distal end to said upper torso support member;

a first push rod journally connected at its proximal end to said first displacement cam and at its distal end to said upper torso support member, said openings defined by said first displacement cam being provided for varying an eccentricity of said first push rod proximal end with respect to said first axle, thereby varying a degree of motion of said upper torso support member; and a second push rod journally connected at its proximal end to said second displacement cam and at its distal end to said lower body support member.

10. The lumbar spine therapy device of claim 9 wherein said degree of motion of each of said upper torso and lower body support members is variable independently one from the other.

11. The device of claim 9 further comprising a mobilization device for enabling said device to be easily transported.

* * * * *